(12) United States Patent
Goswami et al.

(10) Patent No.: US 6,489,763 B1
(45) Date of Patent: Dec. 3, 2002

(54) MAGNET ASSEMBLY FOR NUCLEAR MAGNETIC RESONANCE WELL LOGGING TOOLS

(75) Inventors: Jaideva C. Goswami, Houston, TX (US); Richard W. Oldigs, Huffman, TX (US); Richard P. Harris, Houston, TX (US); Donald C. McKeon, Paris (FR)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/553,462

(22) Filed: Apr. 19, 2000

Related U.S. Application Data

(60) Provisional application No. 60/143,382, filed on Jul. 12, 1999.

(51) Int. Cl.[7] .................................................. G01V 3/00
(52) U.S. Cl. ....................................................... 324/303
(58) Field of Search ........................................ 324/303

(56) References Cited

U.S. PATENT DOCUMENTS

| | | | | |
|---|---|---|---|---|
| 4,717,876 A | * | 1/1988 | Masi et al. ................. | 324/303 |
| 4,717,877 A | * | 1/1988 | Taicher et al. .............. | 324/303 |
| 5,055,788 A | | 10/1991 | Kleinberg et al. | |
| 5,376,884 A | * | 12/1994 | Sezginer ...................... | 324/303 |
| 5,432,446 A | * | 7/1995 | MacInnis et al. ........... | 324/303 |
| 5,486,761 A | * | 1/1996 | Sezginer ...................... | 324/303 |
| 6,348,792 B1 | * | 2/2002 | Beard et al. ................. | 324/300 |
| 6,362,619 B2 | * | 3/2002 | Prammer et al. .......... | 144/134.1 |

OTHER PUBLICATIONS

D. Mckeon, An Improved NMR Tool Design for Faster Logging, May 30, 1999, SPWLA 40th Annual Logging Symposium, pp. 1–14.*

* cited by examiner

*Primary Examiner*—Edward Lefkowitz
*Assistant Examiner*—Dixomara Vargas
(74) *Attorney, Agent, or Firm*—Kevin P. McEnaney; Brigitte L. Jeffery; John J. Ryberg

(57) ABSTRACT

A magnet assembly for nuclear magnetic well logging apparatus includes two diametrically opposed magnets which produce a static and substantially homogeneous magnetic field. Each magnet has a magnet axis and is partitioned into a first and a second magnet segment by a plane substantially parallel to the magnet axis.

15 Claims, 4 Drawing Sheets

MAGNET ASSEMBLY FOR NUCLEAR MAGNETIC RESONANCE WELL LOGGING TOOLS

CROSS REFERENCE TO RELATED APPLICATION

This application claims priority from provisional application serial No. 60/143,382, filed Jul. 12, 1999.

BACKGROUND OF THE INVENTION

1. Technical Field

The invention relates generally to nuclear magnetic resonance (NMR) apparatus and techniques for logging wells. More specifically, the invention relates to a magnet assembly for NMR well logging apparatus.

2. Background Art

NMR is the selective absorption of radio waves by certain atomic nuclei that are immersed in a static magnetic field. The principles of NMR have been used to study the molecular structure of rock formations in oil and gas exploration in a process called well logging. U.S. Pat. No. 5,055,788 issued to Kleinberg et al. discloses an NMR well logging apparatus which includes a magnet array disposed in a tool body and an RF antenna mounted in a recess external to the tool body. The magnet array includes three permanent bar magnets mounted in parallel to each other within the tool body. The magnet array produces a static magnetic field in all regions surrounding the tool, and the antenna produces an oscillating magnetic field which is superposed on the static magnetic field. The volume of investigation, or resonant volume, is an elongated region directly in front of the RF antenna in which the static magnetic field produced by the magnetic array has a saddle point, that is, the region in which the static magnetic field is substantially homogenous and the spatial gradient of the static magnetic field is approximately zero. The tool makes measurements by magnetically tipping the nuclear spins of particles in the formation with a pulse of the oscillating magnetic field, and then detecting the precession of the tipped particles in the static, homogeneous field within the volume of investigation. It should be noted that the depth of investigation is related to the position of the saddle point of the static magnetic field. The further away the saddle point is from the tool face, the greater the depth of investigation, but this is usually at the cost of signal-to-noise ratio.

SUMMARY OF THE INVENTION

One aspect of the invention is a magnet assembly for nuclear magnetic well logging apparatus which comprises two diametrically opposed magnets which produce a static and substantially homogeneous magnetic field. Each magnet has a magnet axis and is partitioned into a first and a second magnet segment by a plane substantially parallel to the magnet axis.

DETAILED DESCRIPTION OF THE INVENTION

Figure 1:
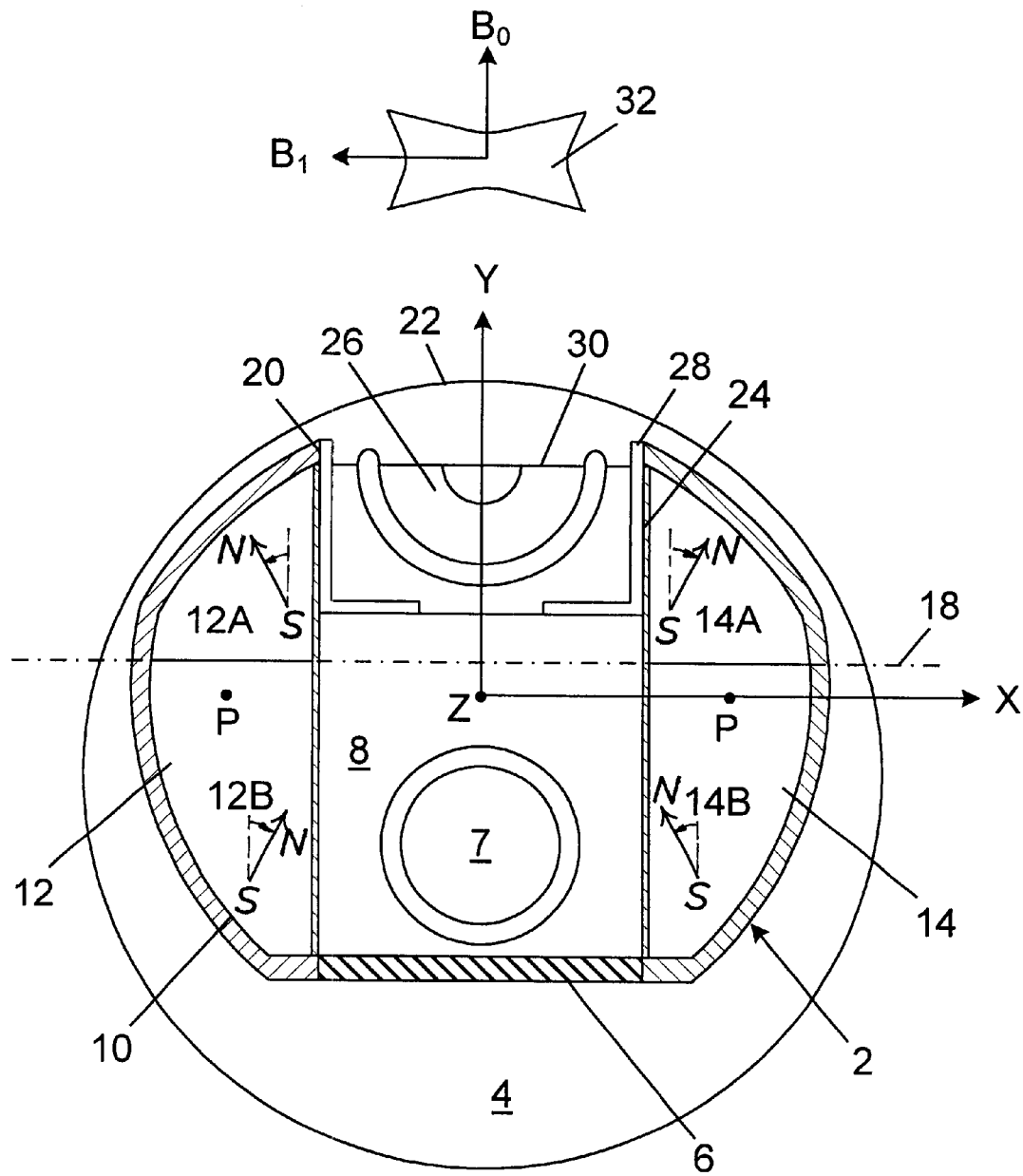
FIG. 1 shows a cross section of an NMR well logging tool.

FIG. 1 shows a cross section of an NMR well logging tool 2 which is disposed in a borehole 4. The logging tool 2 is similar to the logging tool disclosed in U.S. Pat. No. 5,055,788 issued to Kleinberg et al., assigned to Schlumberger Technology Corporation, except for the structure of the magnet assembly which produces the static magnetic field in regions surrounding the tool. The logging tool 2 is movable along a longitudinal axis of the borehole 4. Typically, the logging tool 2 is connected to surface equipment (not shown) by a wireline (not shown). It should be noted that the longitudinal axis of the borehole 4 is in a direction into the paper, i.e., in a direction along the Z-axis. The logging tool 2 includes a tool body 6 which has cavities 7, 8. The tool body 6 may be made of a metal alloy such as steel. The cavity 7 is a longitudinal passage for receiving electrical wiring, which supply power to electronic components (not shown) of the logging tool 2. A magnet assembly 10 is disposed inside the cavity 8. The magnet assembly 10 includes two permanent magnets 12, 14 which are disposed within the cavity 8 in opposed relation and arranged symmetrically about the center of the tool body 6. The cross section of the magnets 12, 14 is not limited to the specific shape shown in FIG. 1 but may have other shapes, e.g., a rectangular shape.

The magnets 12, 14 each have a magnet axis P which is substantially aligned with the longitudinal axis of the borehole 4, i.e., substantially aligned with the Z-axis. The magnet 12 is partitioned into two magnet segments 12A, 12B along a partition plane 18, which is a plane transverse to the XY plane and substantially parallel to the magnet axis P of the magnet 12. The magnet segments 12A, 12B are bonded together with epoxy, although other suitable means for securing the magnets 12A, 12B together may be used. The magnet segment 14 is also partitioned into two magnet segments 14A, 14B along the partition plane 18. The magnet segments 14A, 14B may also be bonded together with epoxy or by other suitable means. The magnet segments 12A, 12B, 14A, 14B are elongated in a direction along the longitudinal axis of the borehole 4, i.e., in a direction along the Z-axis. Each magnet segment may be made of a single permanent magnet or of a plurality of permanent magnets stacked together in a direction along the longitudinal axis of the borehole 4. The magnets 12, 14 should be as strong as practical and should be capable of withstanding physical shock without disintegration. The face 20 of the tool body 6 which faces the borehole wall 22 includes a recess 24 in which an RF antenna 26 is disposed. The recess 24 is lined with a static magnetic shield 28, which protects the antenna 26 from the static magnetic field generated by the magnet assembly 10.

In operation, the magnet assembly 10 generates a static magnetic field $B_0$, and the antenna 26 generates an oscillating magnetic field $B_1$ which is superposed on the static magnetic field $B_0$. The volume of investigation is located in front of the tool face 20 in a region 32 in which the magnetic field $B_0$ produced by the magnetic assembly 10 is substantially homogeneous and the spatial gradient of the magnetic field $B_0$ is approximately zero. The oscillating magnetic field $B_1$ is generally normal to the static magnetic field $B_0$ in the resonant region 32. The logging tool 2 makes measurements by tipping the nuclear spins of particles in the magnetic field $B_0$ within the volume of investigation over time.

Figure 2:
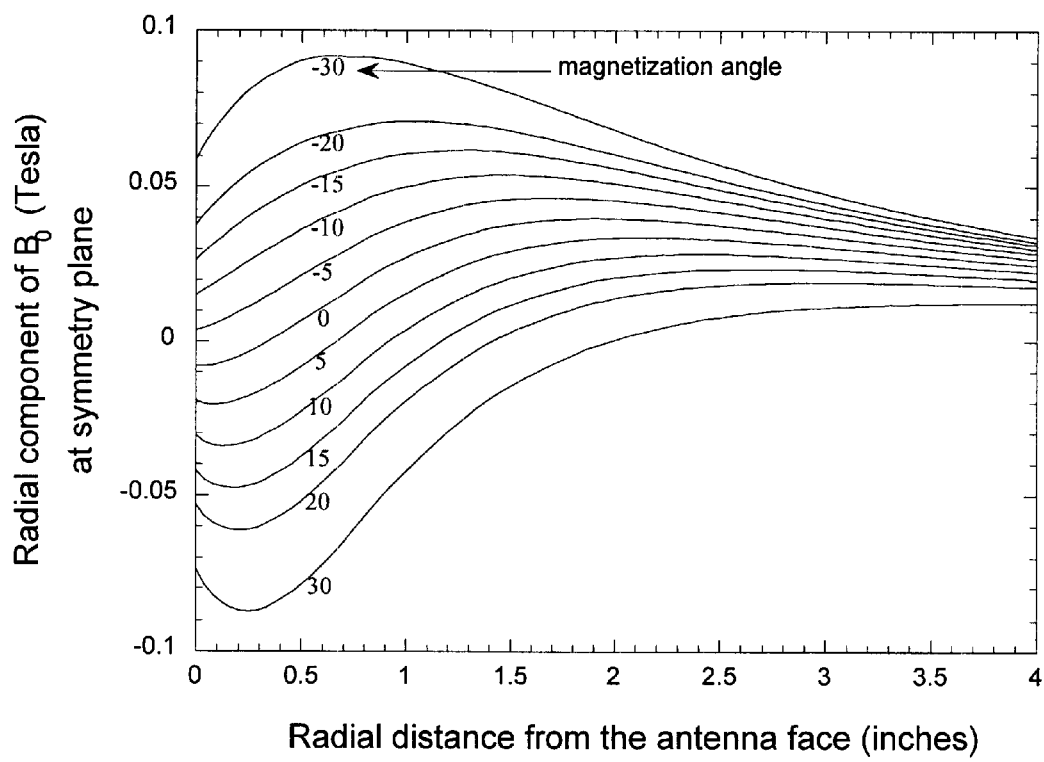
FIG. 2 illustrates the effect of magnetization angle on the magnetic flux density.

FIG. 2 shows a plot of the radial component of the flux density of the magnetic field $B_0$ as a function of the radial distance from the face 30 of the antenna 26, e.g., distance along the Y-axis. For this figure, the magnet segments 12A, 12B, 14A, 14B are magnetized in the same direction. A negative magnetization angle indicates that the magnet segments are magnetized in a direction toward the center of the tool 2, while a positive magnetization angle indicates that the magnet segments are magnetized in a direction away from the center of the tool 2. It is clear from FIG. 2 that as the magnetization angle of the magnetic segments 12A, 12B, 14A, 14B increases, the saddle point, i.e., the resonant region 32, moves away from the tool 2, thus increasing the depth of investigation. However, the strength of the magnetic field $B_0$ decreases as the depth of investigation increases, resulting in a reduction in the signal-to-noise ratio. A finite element model analysis indicates that the operating parameters of the antenna 26 are not influenced by the magnetization angle of the magnetic assembly 10. Therefore, when the magnetization angle is decreased, an increase in the signal-to-noise ratio and a decrease in the depth of investigation are expected.

The performance of the tool 2 is optimized by magnetizing the magnet segments in each magnet 12, 14 with different magnetization angles. For instance, if the upper magnet segments 12A, 14A are magnetized with positive magnetization angles and the lower magnet segments 12B, 14B with negative magnetization angles and the position of the partition plane 18 is properly selected, then the depth of investigation will be primarily determined by the positive magnetization angles while the signal-to-noise ratio will be determined by all the magnet segments. Table 1 illustrates the effect of magnetization angle on the depth of investigation and signal-to-noise ratio. The first two entries in Table 1 are for the embodiment where the magnetization angles of all the magnet segments 12A, 12B, 14A, 14B are −30 and +0 degrees, respectively, with respect to the Y-axis, where the sign indicates the magnetization direction. The third entry corresponds to a scenario where the magnetization angle of the upper magnet segments 12A, 14A is +0 degree and the magnetization angle of the lower magnet segments 12B, 14B is −30 degrees.

TABLE 1

Effect of Magnetization Angle on Depth of Investigation and Signal-to-Noise Ratio

| Magnetization Angle (degrees) | Depth of Investigation (in.) | Signal to Noise Ratio (dB) | Frequency (MHz) |
| --- | --- | --- | --- |
| −30 | 0.57 | 47.84 | 3.964 |
| +0 | 1.90 | 21.62 | 1.716 |
| +0, −30 | 1.41 | 29.62 | 2.312 |

When the magnetization angle of all the magnet segments 12A, 12B, 14A, 14B is +0 degree, with respect to the Y-axis, a good depth of investigation at the cost of signal-to-noise ratio is achieved. However, a combination of positive and negative magnetization angles provides better depth of investigation and better signal-to-noise ratio. It should be clear that the results shown in Table 1 are only for the purpose of illustrating the effect of magnetization angles on depth of investigation and signal-to-noise ratio and are not necessarily the optimized ones. The effect of magnetization angles on the magnet segments shown in Table 1 and FIG. 2 was analyzed using a two-dimensional finite element model program. The length of the volume of investigation, or resonant region, was assumed to be 6 inches.

Figure 3:
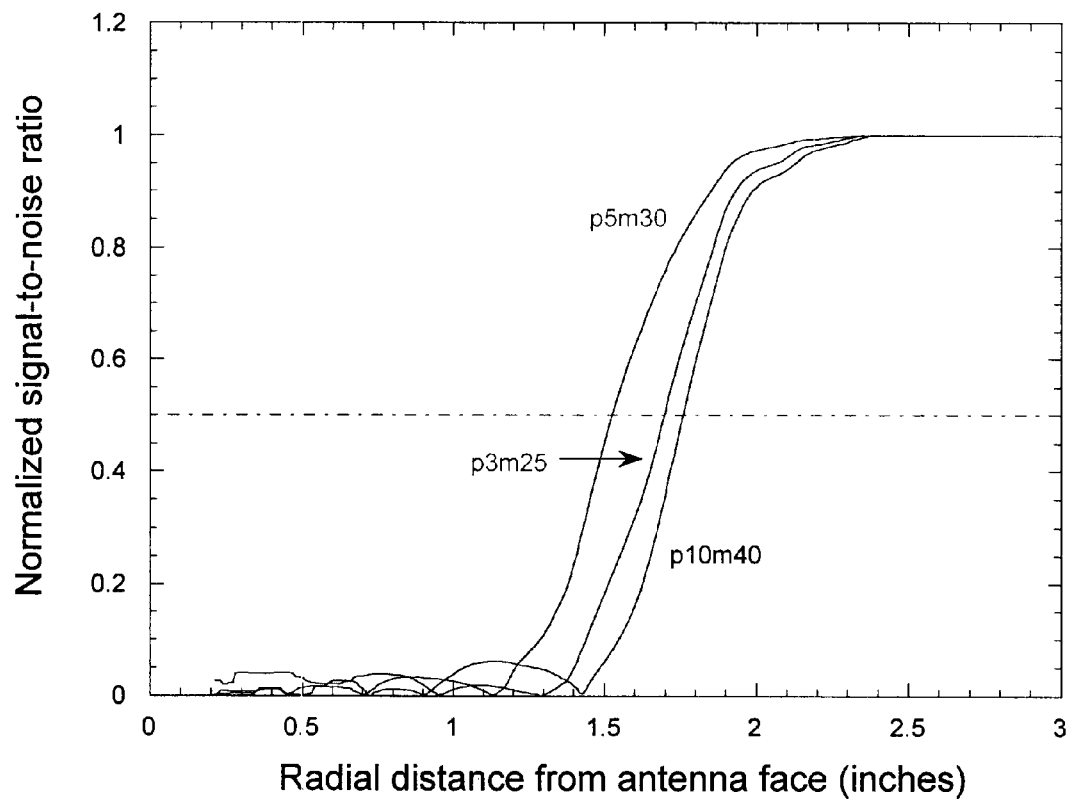
FIG. 3 illustrates the effect of magnetization angle on the performance of the tool shown in FIG. 1.
Figure 4:
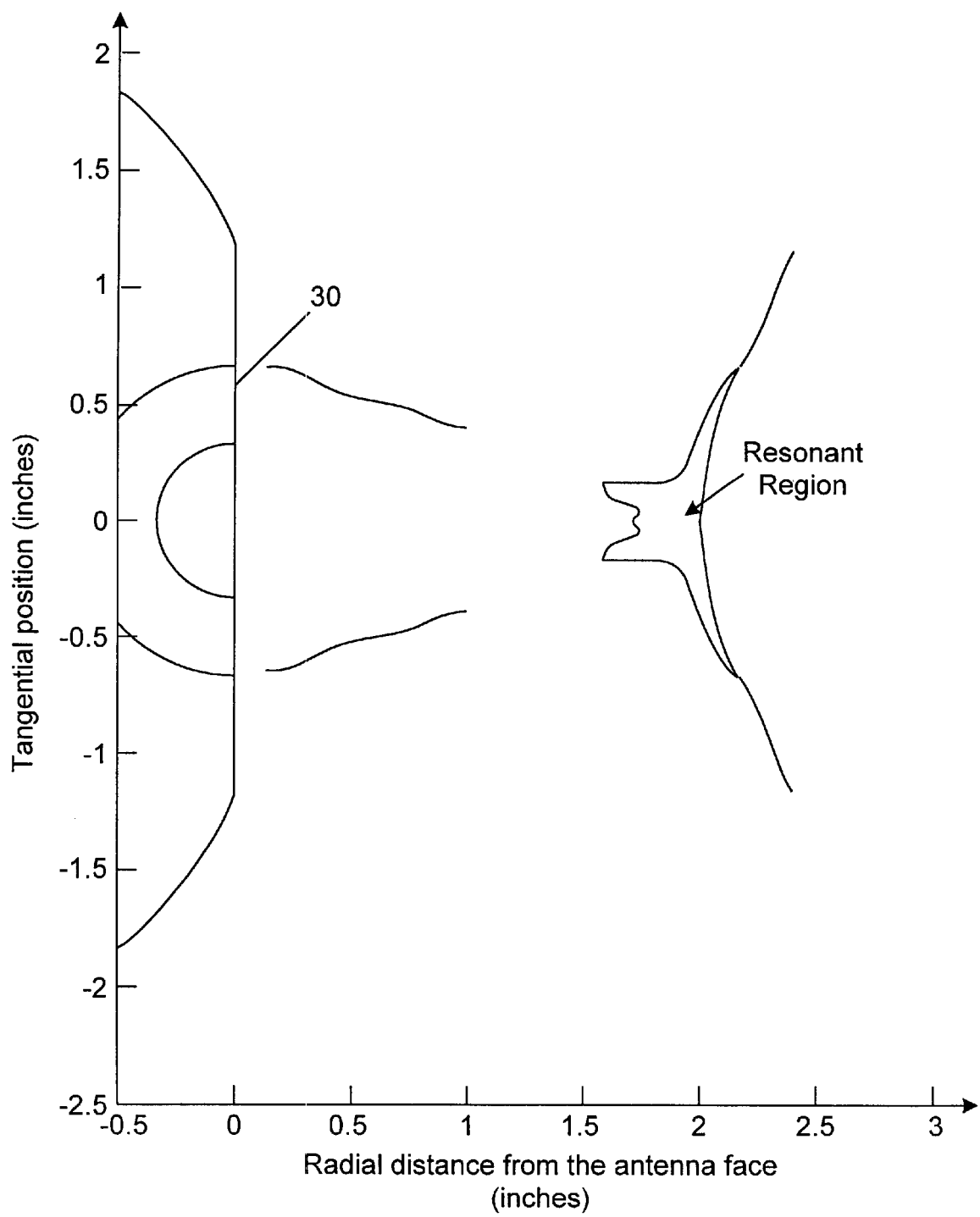
FIG. 4 shows the resonant region in the transverse plane of the tool.

FIG. 3 shows a plot of normalized signal-to-noise ratio as a function of the radial distance from the face 30 of the antenna 26. The numerical values shown in FIG. 3 are obtained through a full three-dimensional electromagnetic modeling of the tool 2. The depth of investigation is defined as the 50% point on the normalized signal-to-noise ratio plot, while the blind zone is defined as the point on the radial axis that corresponds to the maximum magnitude of oscillating signal-to-noise ratio before it starts increasing monotonically. The legends pxxmyy on the plots indicate that the magnetization angles of the upper and the lower magnet segments are +xx and −yy degrees, respectively, with the negative angles pointing towards the center of the tool 2. Table 2 gives the values of the depth of investigation, blind zone, and signal-to-noise ratio for a few combinations of the magnetization angles. FIG. 4 shows a typical view of the volume of investigation, i.e., the resonant region 32, in front of the tool face 20 corresponding to the third entry in Table 2. The width of the RF pulse transmitted by the antenna 26 in this case is 26.95 microseconds.

TABLE 2

Effect of Magnetization Angle on Depth of Investigation, Blind Zone, and Signal-to-Noise Ratio

| Magnet | Depth of Investigation (in.) | Blind Zone (inches, % of maximum) | Signal to Noise ratio (dB) | Frequency (MHz) |
| --- | --- | --- | --- | --- |
| 3, −25 | 1.70 | 0.78 (3.9%) | 30.47 | 2.048 |
| 5, −30 | 1.53 | 0.86 (3.3%) | 30.55 | 2.037 |
| 10, −40 | 1.76 | 1.15 (6.2%) | 27.65 | 1.942 |

The invention provides advantages in that the magnet assembly 10, which includes the partitioned magnets 12, 14, improves the depth of investigation of the logging tool 2. By properly positioning the partition plane 18 in the magnets 12, 14 and by magnetizing the magnet segments in different directions, a high signal-to-noise ratio is also achieved without substantially compromising the improved depth of investigation. It should be noted that each magnet 12, 14 may be partitioned into more than two segments. The performance of the logging tool may also be further enhanced by adjusting the cross sections of the magnets 12, 14 along the partition plane 18, i.e., in a direction along the Z-axis or magnet axis P. It should be noted that the cross sections of the magnets 12, 14 along the partition plane 18 do not have to be uniform.

While the invention has been described with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. A magnet assembly for nuclear magnetic well logging apparatus, comprising:

two diametrically opposed magnets, each magnet having a magnet axis and being partitioned into a first and a second magnet segment along a plane substantially parallel to each magnet axis, the first and second magnet segments having a first and a second magnetization angle whereby a magnetic field of each magnet segment for each diametrically opposed magnets combine to produce a static, non-axisymmetric along a longitudinal axis of the logging apparatus, and substantially homogeneous magnetic field in a resonance region.

2. The magnet assembly of claim 1, wherein each magnet segment is elongated in a direction along the magnet axis.

3. The magnet assembly of claim 1, wherein a magnetization angle of the first magnet segments in a plane transverse to the magnet axis is different from a magnetization angle of the second magnet segments in the same plane.

4. The magnet assembly of claim 3, wherein the magnetization angle of the first segments is in a direction away from the center of the magnet assembly and the magnetization angle of the second segments is in a direction toward the center of the magnet assembly.

5. The magnet assembly of claim 4, wherein the magnetization angle of the first segments is in a direction substantially perpendicular to the center of the magnet assembly.

6. The magnet assembly of claim 1, wherein the magnets comprise permanent magnets.

7. A magnet assembly for nuclear magnetic well logging apparattus, comprising:
two diametrically opposed magnets, each magnet having a magnet axis and being partitioned into a first and a second magnet segment along a plane substantially parallel to the magnet axis, that produce a static, non-axisymmetric, and substantially homogeneous magnetic field;
wherein the magnetization angle of the first magnet segments in a plane transverse to the magnet axis is different from the magnetization angle of the second magnet segments in the same plane.

8. A magnet assembly for nuclear magnetic well logging apparatus, comprising:
two diametrically opposed magnets, each magnet having a magnet axis and being partitioned into a first and a second magnet segment along a plane substantially parallel to each magnet axis, the first and second magnet segments having a first and a second magnetization angle respectively whereby a magnetic field of each magnet segment for each diametrically opposed magnets combine to produce a static, non-axisymmetric along a longitudinal axis of the logging apparatus, and substantially homogeneous magnetic field in a resonance region;
wherein the first magnetization angle is different from the second magnetization angle.

9. The nuclear magnetic resonance well logging apparatus of claim 8, wherein each magnet segment is elongated in a direction along the magnet axis.

10. The nuclear magnetic resonance well logging apparatus of claim 8, wherein a magnetization angle of the first magnet segments in a plane transverse to the magnet axis is different from a magnetization angle of the second magnet segments in the same plane.

11. The nuclear magnetic resonance well logging apparatus of claim 10, wherein the magnetization angle of the first segments is in a direction away from the center of the magnet assembly and the magnetization angle of the second segments is in a direction toward the center of the magnet assembly.

12. The nuclear magnetic resonance well logging apparatus of claim 11, wherein the magnetization angle of the first segments is in a direction substantially perpendicular to the center of the magnet assembly.

13. The nuclear magnetic resonance well logging apparatus of claim 8, wherein the magnets comprise permanent magnets.

14. A nuclear magnetic resonance well logging apparatus including a tool body adapted for longitudinal movement in a borehole, the apparatus comprising:
two diametrically opposed magnets disposed within a cavity in the tool body, each magnet having a magnet axis substantially aligned with the longitudinal axis of the borehole, the magnets producing a static, non-axisymmetric along a longitudinal axis of the logging apparatus, and substantially homogeneous magnetic field in a resonance region in a volume of formation directed to one side of the tool body, each magnet being partitioned into a first and a second magnet segment along a plane substantially parallel to each magnet axis, the first and second magnet segments having a first and a second magnetization angle;
an antenna disposed external to the tool body;
wherein the first magnetization angle is different from the second magnetization angle.

15. A magnet assembly for nuclear magnetic well logging apparatus, comprising:
two diametrically opposed magnets, each magnet having a magnet axis and being partitioned into a first and a second magnet segment along a plane transverse to each magnet axis, the first and second magnet segments having a first and a second magnetization angle whereby a magnetic field of each magnet segment for each diametrically opposed magnets combine to produce a static, non-axisymmetric along a longitudinal axis of the logging apparatus, and substantially homogeneous magnetic field in a resonance region.

* * * * *